(12) United States Patent
Ishino et al.

(10) Patent No.: US 7,314,961 B2
(45) Date of Patent: Jan. 1, 2008

(54) PROCESS FOR PRODUCTION OF ETHERS

(75) Inventors: Hiroshige Ishino, Kurashiki (JP); Hideharu Iwasaki, Kurashiki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 142 days.

(21) Appl. No.: 10/542,890

(22) PCT Filed: Jan. 20, 2004

(86) PCT No.: PCT/JP2004/000401

§ 371 (c)(1),
(2), (4) Date: Aug. 9, 2005

(87) PCT Pub. No.: WO2004/065006

PCT Pub. Date: Aug. 5, 2004

(65) Prior Publication Data

US 2006/0111594 A1 May 25, 2006

(30) Foreign Application Priority Data

Jan. 21, 2003 (JP) ............................. 2003-011847
Aug. 27, 2003 (JP) ............................. 2003-302243

(51) Int. Cl.
*C07C 41/05* (2006.01)
*C07C 41/06* (2006.01)
(52) U.S. Cl. ...................... 568/689; 568/687
(58) Field of Classification Search .................... None
See application file for complete search history.

(56) References Cited

U.S. PATENT DOCUMENTS 3,670,032 A 6/1972 Romanelli
5,198,598 A * 3/1993 Hill et al. .................. 568/619
5,886,211 A 3/1999 Hirai et al.

2005/0038273 A1 2/2005 Rottger et al.

FOREIGN PATENT DOCUMENTS

DE 101 28 144 A1 12/2002
EP 0 542 366 A1 5/1993
JP 04-327595 A 11/1992

OTHER PUBLICATIONS

Herrmann, *Angew. Chem. Int. Ed.*, 41: 1290-1309 (2002).
Herrmann et al., *Advances in Organometallic Chemistry*, 48: 42-47 (2001).
Hillier et al., *Platinum Metals Rev.*, 46(2): 50-64 (2002).
Jackstell et al., *Angew. Chem. Int. Ed.*, 41(6): 986-989 (2002).
Jackstell et al., *Journal of Molecular Catalysis A: Chemical*, 185: 105-112 (2002).
Tsuji, "Dimerization and Telomerization of Conjugated Dienes and Related Reactions," *Palladium Reagents and Catalysts: Innovations in Organic Synthesis*, pp. 423-441 (Chichester: John Wiley & Sons, 1995).

* cited by examiner

*Primary Examiner*—Yvonne Eyler
*Assistant Examiner*—Yevgeny Valenrod
(74) *Attorney, Agent, or Firm*—Leydig, Voit & Mayer, Ltd.

(57) ABSTRACT

According to the present invention, a method of producing ethers, which includes subjecting a conjugated diene compound and an alcohol to a telomerization reaction in the presence of a composition containing a palladium compound, an isocyanide represented by the formula (I)

$$R^1R^2R^3CNC \qquad (I)$$

and a base represented by the formula (II)

$$M(OR^4)_n \qquad (II)$$

as a catalyst is provided. According to the method of the present invention, by telomerization reaction of a conjugated diene compound and an alcohol, ethers can be produced industrially advantageously. (In the above-mentioned formulas, each symbol is as defined in the specification.)

7 Claims, No Drawings

PROCESS FOR PRODUCTION OF ETHERS

CROSS-REFERENCE TO RELATED PATENT APPLICATION

This application is the U.S. national phase of International Patent Application No. PCT/JP2004/00401, which was filed on Jan. 20, 2004.

TECHNICAL FIELD

The present invention relates to a method of producing ethers, which comprises subjecting a conjugated diene compound and an alcohol to a telomerization reaction, and a composition having a catalytic function, which is to be used for this method.

Ethers produced by the present invention are useful for starting materials of various polymer, and for intermediates of flavors and the like.

BACKGROUND ART

A telomerization reaction of a conjugated diene compound means an oligomerization reaction of a conjugated diene compound upon intake of a nucleophilic reactant. For example, a reaction wherein 2 molecules of butadiene react with 1 molecule of a compound having an active hydrogen such as acetic acid and the like to give a product such as 1-acetoxy-2,7-octadiene and the like can be mentioned.

It is known that a palladium complex, particularly, a palladium complex coordinating phosphines shows a superior activity as a catalyst for telomerization reaction of a conjugated diene compound [see, for example, *Palladium Reagents and Catalysts*, Written by Jiro Tsuji, Published by John Wiley & Sons, pp. 423-441 (1995)]. However, use of a palladium complex coordinating phosphines as a catalyst for industrial telomerization reaction is associated with the following problems. (1) A palladium complex coordinating phosphines shows poor thermal stability, and when a telomerization product and a catalyst component are separated by evaporation, the complex is decomposed during the step to precipitate palladium metal. As a result, the catalyst cannot be reused easily and the precipitated metal causes problems of piping blockage and the like. (2) To maintain thermal stability of the palladium complex coordinating phosphines, the reaction mixture should contain an excess amount of phosphine per 1 atom of the palladium. While the presence of an excess amount of phosphine enhances the stability of the palladium complex coordinating phosphines, it degrades the catalytic activity. Moreover, problems such as decrease of the concentration of phosphine due to the production of phosphine oxide as a result of the oxidization of the excess phosphine, degraded catalytic activity and the like occur. From the above aspects, a compound having a coordinating property to a metal such as palladium and the like and exhibiting a telomerization reactivity has been demanded as a ligand replacing phosphine.

A method has been reported wherein a conjugated diene compound having 4 to 6 carbon atoms and a mono-alcohol are telomerized in the presence of a catalyst system comprising isocyanide, which is a non-phosphine type ligand, and a nickel compound to give unsaturated ether [see, for example, U.S. Pat. No. 3,670,029]. In Examples thereof, a telomerization reaction of 1,3-butadiene and methanol is carried out in the presence of a catalyst system comprising bis (1,5-cyclooctadiene) nickel and cyclohexylisocyanide [0.001-0.01 equivalent of bis (1,5-cyclooctadiene) nickel relative to 1,3-butadiene], whereby 1-methoxy-2,7-octadiene and 3-methoxy-1,7-octadiene are obtained at a ratio of 91:9 (weight ratio).

When a catalyst system comprising a nickel compound and isocyanide is used for telomerization reaction of a conjugated diene compound and alcohol, the terminal-position selectivity of the alcohol-addition product is about 90% at the highest. Since the yield of substantial 1-position substituted ether is low and the catalytic activity is low, a large amount of catalyst is necessary, thus insufficient in the industrial method.

In addition, a telomerization reaction using a palladium catalyst comprising nitrogen-containing heterocyclic carbene as a non-phosphine ligand has been reported [see, for example, DE 10128144 A1 and *Angew. Chem. Int. Ed.*, vol. 41, pp. 1290-1309 (2002)]. A nitrogen-containing heterocyclic carbene has high electron-donating property and firmly binds with a metal. A metal coordinating with the nitrogen-containing heterocyclic carbene shows a remarkably increased electron density. Therefore, a palladium complex coordinating nitrogen-containing heterocyclic carbene is superior in thermal stability and shows superior catalytic activity in oxidative addition reaction and the like. Such palladium complex is known to be usable as a catalyst of coupling reactions such as Mizorogi-Heck reaction using aryl chloride, Suzuki-Miyaura coupling reaction and the like [see, for example, *Platinum Metals Rev.*, vol. 46, pp. 50-64 (2002) and *Advances in Organometallic Chemistry*, vol. 48, pp. 42-47 (2002)]. It has been reported that, when this complex is used as a catalyst of telomerization of 1,3-butadiene and methanol, the complex shows superior productivity (TON, turnover number), selectivity of terminal-position of the methanol addition product and telomerization selectivity, as compared to a palladium complex coordinating phosphine [see, for example, *Angew. Chem. Int. Ed.*, vol. 41, pp. 986-989 (2002) and *Journal of Molecular Catalysis A*: Chemical, vol. 185, pp. 105-112 (2002)].

In telomerization using a palladium complex coordinating nitrogen-containing heterocyclic carbene, as mentioned above, the rate of an oxidative coupling reaction of 2 molecules of a conjugated diene compound increases due to the electron-donating property of the nitrogen-containing heterocyclic carbene, but the rate of a reductive elimination reaction becomes slow. To enhance reaction efficiency, an excess base needs to be added to the palladium complex coordinating nitrogen-containing heterocyclic carbene. Consequently, a problem occurs in that the stability of a palladium complex coordinating nitrogen-containing heterocyclic carbene cannot be maintained easily. Moreover, it is assumed that, when such telomerization is industrially performed and the catalyst is circulated for reuse, the catalytic activity will be degraded, and serious problems of corrosion of reaction reactor, piping blockage due to precipitation of a base and the like will be produced. An additional problem is expected in that the cost of ligand becomes high because several steps are required to separately synthesize nitrogen-containing heterocyclic carbene to be used as a ligand.

Furthermore, a telomerization reaction using a palladium catalyst, wherein isocyanide is used as a non-phosphine ligand, has been reported (see, for example, JP S48-43327 B, U.S. Pat. No. 3,670,032). In an Example therein, a telomerization reaction of 1,3-butadiene and trimethylolpropane is carried out in the presence of a catalyst system of tetrakis (triphenylphosphine)palladium and cyclohexylisocyanide. However, the ratio of tetrakis (triphenylphosphine)palladium as the catalyst and butadiene used, yield of the product, reaction time and the like are not described but it has been only reported that octadienyldihydroxymethylbutane was obtained as a main product. The present inventors have found that when an isocyanide having hydrogen on the carbon at the α-position thereof is used as a ligand, the hydrogen is eliminated by a base used for the telomerization reaction, thus resulting in the decomposition of isocyanide and a failure to show an intended function of a ligand, and the object function as a telomerizing catalyst ligand is markedly degraded (below-mentioned Comparative Example 2). In the reported Example, moreover, isocyanide is concurrently used with a palladium catalyst already having phosphorus ligands. The present inventors have found problems associated with the use of a palladium already having phosphorus ligands, in that it suppresses coordination of isocyanide, thereby markedly lowering the rate of the reaction, and degrades the regioselectivity of alcohol in nucleophilic reaction (below-mentioned Comparative Example 3), and therefore, the terminal-position selectivity, i.e. straight chain selectivity of alcohol addition becomes low. The present inventors have also found a problem in that the amount of a catalyst to be used per butadiene cannot be reduced, or the conversion ratio of butadiene cannot be increased, because coordination of phosphorus prevents sufficient increase in the charge density on palladium.

DISCLOSURE OF THE INVENTION

It is therefore an object of the present invention to provide a composition used for a telomerization reaction of a conjugated diene compound and an alcohol, which expresses high catalytic activity, and which affords an alcohol addition product with high selectivity of terminal-position (straight chain selectivity) at a low cost.

Another object of the present invention is to provide a method of producing ethers industrially advantageously by a telomerization reaction of a conjugated diene compound and an alcohol using the above-mentioned composition.

Accordingly, the present invention relates to a composition comprising a palladium compound, an isocyanide represented by the formula (I)

$$R^1R^2R^3CNC \qquad (I)$$

wherein $R^1$, $R^2$ and $R^3$ are the same or different and each is an optionally substituted alkyl group, an optionally substituted alkenyl group, an optionally substituted aryl group or an optionally substituted aralkyl group, or two of them optionally form a cycloalkyl group together with a carbon atom bonded thereto

[hereinafter this is to be referred to as isocyanide (I)], and a base represented by the formula (II)

$$M(OR^4)_n \qquad (II)$$

wherein M is an alkali metal, an alkaline earth metal or an onium, $R^4$ is a hydrogen atom, an optionally substituted alkyl group, an optionally substituted alkenyl group, an optionally substituted aryl group or an optionally substituted aralkyl group, when M is an alkali metal or an onium, then n is 1, and when M is an alkaline earth metal, then n is 2,

[hereinafter this is to be referred to as base (II)].

The present invention relates to a production method of ethers, which comprises subjecting a conjugated diene compound and an alcohol to a telomerization reaction in the presence of the above-mentioned composition as a catalyst to give an ether.

The composition of the present invention is provided at a low cost, expresses high catalytic activity in a telomerization reaction of a conjugated diene compound and an alcohol, and affords an alcohol addition product with high straight chain selectivity.

According to the method of the present invention, ethers can be produced industrially advantageously from a conjugated diene compound and an alcohol. According to the method of the present invention, moreover, linear ethers wherein alcohols have been added to the terminal can be produced industrially advantageously.

BEST MODE FOR EMBODYING THE INVENTION

The palladium compound is not particularly limited as long as it does not have strong coordinating property as phosphorus compounds have and, for example, a divalent palladium salts such as palladium formate, palladium acetate, palladium chloride, palladium bromide, palladium carbonate, palladium sulfate, palladium nitrate, palladium acetylacetonate, bis(benzonitrile)palladium dichloride, bis(t-butylisocyanide)palladium dichloride, sodium tetrachloropalladate, potassium tetrachloropalladate and the like, bis(dibenzylideneacetone) palladium, tris(dibenzylideneacetone)dipalladium, bis(1,5-cyclooctadiene)palladium and the like can be mentioned. As the palladium compound to be used in combination with an isocyanide (I), a divalent palladium compound is more preferable than a 0-valent palladium compound in view of antioxidative stability and industrial availability, and a divalent palladium salt is particularly preferable in view of superior catalytic activity, selectivity of terminal-position (straight chain selectivity) of alcohol addition and telomerization selectivity.

The isocyanide (I) is also referred to as isonitrile or carbylamine, and produced easily and economically from the corresponding amine.

In the formula (I) representing isocyanides (I), the alkyl group for $R^1$, $R^2$ or $R^3$ may be a straight chain, branched chain or cyclic alkyl group, and an alkyl group having 1 to 8 carbon atoms is preferable, such as methyl group, ethyl group, propyl group, isopropyl group, butyl group, isobutyl group, s-butyl group, t-butyl group, pentyl group, 1,1-dimethylpropyl group, hexyl group, heptyl group, octyl group, 1,1,3,3-tetramethylbutyl group, cyclopentyl group, cyclohexyl group, cycloheptyl group, cyclooctyl group and the like. The alkenyl group may be a straight chain, branched chain or cyclic alkenyl group, and an alkenyl group having 2 to 8 carbon atoms is preferable. For example, vinyl group, allyl group, crotyl group, prenyl group, 5-hexenyl group, 6-heptenyl group, 7-octenyl group, cyclohexenyl group, cyclooctenyl group and the like can be mentioned. These alkyl groups and alkenyl groups optionally have an atom besides hydrogen atom or a functional group on the carbon atom. As the atom besides hydrogen atom, for example, a halogen atom such as fluorine atom, chlorine atom, bromine atom, iodine atom and the like, and the like can be mentioned. As the functional group, for example, an alkoxyl group such as methoxy group, ethoxy group, isopropoxy group and the like (preferably alkoxyl group having 1 to 8 carbon atoms); amino group; cyano group; hydroxyl group; keto group (oxo group); carboxyl group and the like can be mentioned.

As the aryl group for $R^1$, $R^2$ or $R^3$, an aryl group having 6 to 20 carbon atoms is preferable, such as phenyl group, naphthyl group, indenyl group, phenanthryl group, anthracenyl group, tetracenyl group and the like. As the aralkyl group, an aralkyl group having 7 to 20 carbon atoms is preferable, such as benzyl group, naphthylmethyl group, indenylmethyl group, biphenylylmethyl group and the like.

These aryl groups and aralkyl groups optionally have an atom besides hydrogen atoms, a substituent or a functional group on the carbon atom. As the atom besides hydrogen atoms, for example, a halogen atom such as fluorine atom, chlorine atom, bromine atom, iodine atom and the like, and the like can be mentioned. As the substituent on the ring, for example, an alkyl group having 1 to 8 carbon atoms such as methyl group, ethyl group, propyl group, isopropyl group, butyl group, isobutyl group, s-butyl group, t-butyl group, pentyl group, hexyl group, heptyl group, octyl group, cyclopentyl group, cyclohexyl group, cycloheptyl group, cyclooctyl group and the like; an alkenyl group having 2 to 8 carbon atoms such as vinyl group, allyl group, crotyl group, prenyl group, 5-hexenyl group, 6-heptenyl group, 7-octenyl group, cyclohexenyl group, cyclooctenyl group and the like; an aryl group having 6 to 20 carbon atoms such as phenyl group, tolyl group, xylyl group, cumenyl group, mesityl group, 2,6-diisopropylphenyl group, naphthyl group, indenyl group, biphenylyl group, biphenylenyl group, phenanthryl group, anthracenyl group, tetracenyl group and the like; an aralkyl group having 7 to 20 carbon atoms such as benzyl group, naphthylmethyl group, indenylmethyl group, biphenylylmethyl group and the like, and the like can be mentioned. As the functional group, for example, an alkoxyl group such as methoxy group, ethoxy group, isopropoxy group and the like (preferably an alkoxyl group having 1 to 8 carbon atoms); amino group; cyano group; hydroxyl group; keto group; carboxyl group and the like can be mentioned.

As the cycloalkyl group formed by two of $R^1$, $R^2$ and $R^3$ together with the carbon atom bonded thereto, for example, cyclopropyl group, cyclobutyl group, cyclopentyl group, cyclohexyl group, cycloheptyl group, cyclooctyl group and the like can be mentioned.

As representative examples of the isocyanide (I), for example, t-butylisocyanide, 1,1-dimethylpropylisocyanide, 1-methylcyclohexylisocyanide, 1,1,3,3-tetramethylbutylisocyanide, 1,1-dimethylbenzylisocyanide and the like can be mentioned. As the isocyanide (I), an isocyanide wherein the group represented by $R^1R^2R^3C—$ is a tertiary alkyl group having 4 to 8 carbon atoms is preferable, and t-butylisocyanide, 1,1-dimethylpropylisocyanide, 1,1,3,3-tetramethylbutylisocyanide are more preferable.

In the formula (II) showing base (II), as the alkali metal for M, for example, lithium, sodium, potassium, rubidium, cesium and the like can be mentioned, as the alkaline earth metal, for example, magnesium, calcium, strontium, barium and the like can be mentioned. As the onium for M, for example, ammonium, sulfonium, phosphonium, oxonium and the like can be mentioned.

As the above-mentioned ammonium, an ammonium represented by the following the formula (III)

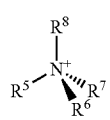

(III)

wherein $R^5$, $R^6$, $R^7$ and $R^8$ each represents hydrogen atom, an optionally substituted alkyl group, an optionally substituted alkenyl group, an optionally substituted aryl group or an optionally substituted aralkyl group, is preferable.

As the above-mentioned sulfonium, a sulfonium represented by the following the formula (IV)

(IV)

wherein $R^9$, $R^{10}$ and $R^{11}$ each represents hydrogen atom, an optionally substituted alkyl group, an optionally substituted alkenyl group, an optionally substituted aryl group or an optionally substituted aralkyl group, is preferable.

As the above-mentioned phosphonium, a phosphonium represented by the following the formula (V)

(V)

wherein $R^{12}$, $R^{13}$, $R^{14}$ and $R^{15}$ each represents hydrogen atom, an optionally substituted alkyl group, an optionally substituted alkenyl group, an optionally substituted aryl group or an optionally substituted aralkyl group, is preferable.

As the above-mentioned oxonium, an oxonium represented by the following the formula (VI)

(VI)

wherein $R^{16}$, $R^{17}$ and $R^{18}$ each represents hydrogen atom, an optionally substituted alkyl group, an optionally substituted alkenyl group, an optionally substituted aryl group or an optionally substituted aralkyl group, is preferable.

In the above-mentioned formula, the alkyl group for $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ or $R^{18}$ is a straight chain, branched chain or cyclic alkyl group, and an alkyl group having 1 to 8 carbon atoms such as methyl group, ethyl group, propyl group, isopropyl group, butyl group, isobutyl group, s-butyl group, t-butyl group, pentyl group, hexyl group, heptyl group, octyl group, cyclopentyl group, cyclohexyl group, cycloheptyl group, cyclooctyl group and the like are preferable. The alkenyl group may be a straight chain, branched chain or cyclic alkenyl group, and an alkenyl group having 2 to 8 carbon atoms such as vinyl group, allyl group, crotyl group, prenyl group, 5-hexenyl group, 6-heptenyl group, 7-octenyl group, cyclohexenyl group, cyclooctenyl group and the like are preferable. These alkyl groups and alkenyl groups optionally have an atom besides hydrogen atoms or a functional group on the carbon atom. As the atom besides hydrogen atoms, for example, a halogen atom such as fluorine atom, chlorine atom, bromine atom, iodine atom and the like, and the like can be mentioned. As the functional group, for example, an alkoxyl group such as methoxy group, ethoxy group, isopropoxy group and the like (preferably an alkoxyl group having 1 to 8 carbon atoms); amino group; cyano group; hydroxyl group; keto group; carboxyl group and the like can be mentioned.

As the aryl group for $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ or $R^{18}$, an aryl group having 6 to 20 carbon atoms such as phenyl group, naphthyl group, indenyl group, phenanthryl group, anthracenyl group, tetracenyl group and the like are preferable. As the aralkyl group, an aralkyl group having 7 to 20 carbon atoms such as benzyl group, naphthylmethyl group, indenylmethyl group, biphenylylmethyl group and the like are preferable. These aryl groups and aralkyl groups optionally have an atom besides hydrogen atoms, a substituent or a functional group on the carbon atom. As the atom besides hydrogen atoms, for example, a halogen atom such as fluorine atom, chlorine atom, bromine atom, iodine atom and the like, and the like can be mentioned. As the substituent on the ring, for example, an alkyl group having 1 to 8 carbon atoms such as methyl group, ethyl group, propyl group, isopropyl group, butyl group, isobutyl group, s-butyl group, t-butyl group, pentyl group, hexyl group, heptyl group, octyl group, cyclopentyl group, cyclohexyl group, cycloheptyl group, cyclooctyl group and the like; an alkenyl group having 2 to 8 carbon atoms such as vinyl group, allyl group, crotyl group, prenyl group, 5-hexenyl group, 6-heptenyl group, 7-octenyl group, cyclohexenyl group, cyclooctenyl group and the like; an aryl group having 6 to 20 carbon atoms such as phenyl group, tolyl group, xylyl group, cumenyl group, mesityl group, 2,6-diisopropylphenyl group, naphthyl group, indenyl group, biphenylyl group, biphenylenyl group, phenanthryl group, anthracenyl group, tetracenyl group and the like; an aralkyl group having 7 to 20 carbon atoms such as benzyl group, naphthylmethyl group, indenylmethyl group, biphenylylmethyl group and the like, and the like can be mentioned. As the functional group, for example, an alkoxyl group such as methoxy group, ethoxy group, isopropoxy group and the like (preferably an alkoxyl group having 1 to 8 carbon atoms); amino group; cyano group; hydroxyl group; keto group; carboxyl group and the like can be mentioned.

As representative examples of the ammonium, tetramethylammonium, tetraethylammonium, tetra-n-propylammonium, triisopropylammonium, tetra-n-butylammonium, benzyltrimethylammonium and the like can be mentioned.

As representative examples of the sulfonium, trimethylsulfonium, triethylsulfonium, tri-n-propylsulfonium, triisopropylsulfonium and the like can be mentioned.

As representative examples of the phosphonium, tetramethylphosphonium, tetraethylphosphonium, tetra-n-propylphosphonium, triisopropylphosphonium ion, tetra-n-butylphosphonium, benzyltrimethylphosphonium ion, tetraphenylphosphonium and the like can be mentioned.

As representative examples of the oxonium, trimethyloxonium, triethyloxonium, tri-n-propyloxonium, triisopropyloxonium and the like can be mentioned.

In the formula (II) showing base (II), as the alkyl group for $R^4$ may be a straight chain, branched chain or cyclic alkyl group, and an alkyl group having 1 to 8 carbon atoms such as methyl group, ethyl group, propyl group, isopropyl group, butyl group, isobutyl group, s-butyl group, t-butyl group, pentyl group, hexyl group, heptyl group, octyl group, cyclopentyl group, cyclohexyl group, cycloheptyl group, cyclooctyl group and the like are preferable. As the alkenyl group, an alkenyl group having 2 to 8 carbon atoms is preferable, which may be a straight chain, branched chain or cyclic alkenyl group. Examples thereof include vinyl group, allyl group, crotyl group, prenyl group, 5-hexenyl group, 6-heptenyl group, 7-octenyl group, cyclohexenyl group, cyclooctenyl group and the like. These alkyl groups and alkenyl groups optionally have an atom besides hydrogen atoms or a functional group on the carbon atom. As the atom besides hydrogen atoms, for example, a halogen atom such as fluorine atom, chlorine atom, bromine atom, iodine atom and the like, and the like can be mentioned. As the functional group, for example, an alkoxyl group such as methoxy group, ethoxy group, isopropoxy group and the like (preferably an alkoxyl group having 1 to 8 carbon atoms); amino group; cyano group; hydroxyl group; keto group; carboxyl group and the like can be mentioned.

As the aryl group for $R^4$, an aryl group having 6 to 20 carbon atoms, such as phenyl group, naphthyl group, indenyl group, phenanthryl group, anthracenyl group, tetracenyl group and the like are preferable. As the aralkyl group, an aralkyl group having 7 to 20 carbon atoms such as benzyl group, naphthylmethyl group, indenylmethyl group, biphenylylmethyl group and the like are preferable. These aryl groups and aralkyl groups optionally have an atom besides hydrogen atoms, a substituent or a functional group on the carbon atom. As the atom besides hydrogen atoms, for example, a halogen atom such as fluorine atom, chlorine atom, bromine atom, iodine atom and the like, and the like can be mentioned. As the substituent on the ring, for example, an alkyl group having 1 to 8 carbon atoms such as methyl group, ethyl group, propyl group, isopropyl group, butyl group, isobutyl group, s-butyl group, t-butyl group, pentyl group, hexyl group, heptyl group, octyl group, cyclopentyl group, cyclohexyl group, cycloheptyl group, cyclooctyl group and the like; an alkenyl group having 2 to 8 carbon atoms such as vinyl group, allyl group, crotyl group, prenyl group, 5-hexenyl group, 6-heptenyl group, 7-octenyl group, cyclohexenyl group, cyclooctenyl group and the like; an aryl group having 6 to 20 carbon atoms such as phenyl group, tolyl group, xylyl group, cumenyl group, mesityl group, 2,6-diisopropylphenyl group, naphthyl group, indenyl group, biphenylyl group, biphenylenyl group, phenanthryl group, anthracenyl group, tetracenyl group and the like; an aralkyl group having 7 to 20 carbon atoms such as benzyl group, naphthylmethyl group, indenylmethyl group, biphenylylmethyl group and the like, and the like can be mentioned. As the functional group, for example, an alkoxyl group such as methoxy group, ethoxy group, isopropoxy group and the like (preferably an alkoxyl group having 1 to 8 carbon atoms); amino group; cyano group; hydroxyl group; keto group; carboxyl group and the like can be mentioned.

As the base (II), for example, lithium hydroxide, lithium methoxide, sodium hydroxide, sodium methoxide, sodium isopropoxide, sodium s-butoxide, sodium phenoxide, sodium benzyloxide, potassium hydroxide, potassium methoxide, potassium ethoxide, potassium isopropoxide, potassium s-butoxide, potassium t-butoxide, potassium phenoxide, potassium benzyloxide, rubidium hydroxide, cesium hydroxide, calcium hydroxide, strontium hydroxide, barium hydroxide, tetramethylammonium hydroxide, tetramethylammonium methoxide, tetramethylammonium phenoxide, tetramethylammonium benzyloxide, tetrabutylammonium hydroxide, benzyltrimethylammonium hydroxide, trimethylsulfonium hydroxide, tetraphenylphosphonium hydroxide, trimethyloxonium hydroxide and the like can be mentioned.

As mentioned above, the composition of the present invention comprises a palladium compound, isocyanide (I) and base (II), and expresses a superior catalytic activity in a telomerization reaction system. The composition ratio of isocyanide (I) is preferably within the range of 0.1-50 equivalents, more preferably 1-20 equivalents, relative to the palladium compound. When the composition ratio of isocyanide (I) exceeds 50 equivalents relative to the palladium compound, the coordination of the conjugated diene compound to the palladium compound is inhibited by the isocyanide (I), and the rate of the telomerization reaction decreases. The composition ratio of the base (II) is preferably within the range of 0.1-100000 equivalents, more preferably 1-10000 equivalents, relative to the palladium compound.

As the conjugated diene compound to be subjected to the telomerization reaction in the present invention, for example, 1,3-butadiene and a 2- and/or 3-substituted derivative thereof and a mixture thereof can be mentioned. As the substituent at the 2-position or the 3-position, an alkyl group or a halogen atom can be mentioned. The alkyl group may be a straight chain, branched chain or cyclic alkyl group, and an alkyl group having 1 to 20 carbon atoms such as methyl group, ethyl group, propyl group, isopropyl group, butyl group, isobutyl group, s-butyl group, t-butyl group, octyl group, dodecyl group, octadecyl group, cyclopentyl group, cyclohexyl group, cyclooctyl group, cyclododecyl group and the like are preferable, particularly, a methyl group is preferable. As the halogen atom, a chlorine atom is preferable.

As representative examples of the conjugated diene compound, 1,3-butadiene, isoprene, piperylene, 2,3-dimethyl-1,3-butadiene, 1,3,7-octatriene, 1,3-cyclohexadiene, 1,3-cyclooctadiene and the like can be mentioned. As the conjugated diene compound, a non-cyclic diene compound having 4 to 6 carbon atoms is preferable, and 1,3-butadiene is more preferable.

The alcohol to be used in the present invention is represented by the following the formula (VII)

R$^{19}$OH　　　　　　　　(VII)

wherein R$^{19}$ is an optionally substituted alkyl group, an optionally substituted alkenyl group, an optionally substituted aryl group or an optionally substituted aralkyl group.

In the above-mentioned formula, the alkyl group for R$^{19}$ may be a straight chain, branched chain or cyclic alkyl group, and an alkyl group having 1 to 8 carbon atoms such as methyl group, ethyl group, propyl group, isopropyl group, butyl group, isobutyl group, s-butyl group, t-butyl group, pentyl group, hexyl group, heptyl group, octyl group, cyclopentyl group, cyclohexyl group, cycloheptyl group, cyclooctyl group and the like are preferable. The alkenyl group may be a straight chain, branched chain or cyclic alkenyl group, and an alkenyl group having 2 to 8 carbon atoms such as vinyl group, allyl group, crotyl group, prenyl group, 5-hexenyl group, 6-heptenyl group, 7-octenyl group, cyclohexenyl group, cyclooctenyl group and the like are preferable. These alkyl groups and alkenyl group optionally have an atom besides hydrogen atoms or a functional group on the carbon atom. As the atom besides hydrogen atoms, for example, a halogen atom such as fluorine atom, chlorine atom, bromine atom, iodine atom and the like, and the like can be mentioned. As the functional group, for example, an alkoxyl group such as methoxy group, ethoxy group, isopropoxy group and the like (preferably an alkoxyl group having 1 to 8 carbon atoms); amino group; cyano group; hydroxyl group; keto group; carboxyl group; hydroxyalkoxyl group such as hydroxymethoxy group, 2-hydroxyethoxy group and the like (preferably a hydroxyalkoxyl group having 1 to 8 carbon atoms); an alkoxyalkoxyl group such as 2-methoxyethoxy group, 2-ethoxyethoxy group and the like (preferably a C$_{1-8}$ alkoxy C$_{1-8}$ alkoxyl group) and the like can be mentioned.

As the aryl group for R$^{19}$, an aryl group having 6 to 20 carbon atoms such as phenyl group, naphthyl group, indenyl group, phenanthryl group, anthracenyl group, tetracenyl group and the like are preferable. As the aralkyl group, an aralkyl group having 7 to 20 carbon atoms such as benzyl group, naphthylmethyl group, indenylmethyl group, biphenylylmethyl group and the like are preferable. These aryl groups and aralkyl groups optionally have an atom besides hydrogen atoms, a substituent or a functional group on the carbon atom. As the atom besides hydrogen atoms, for example, a halogen atom such as fluorine atom, chlorine atom, bromine atom, iodine atom and the like, and the like can be mentioned. As the substituent on the ring, for example, an alkyl group having 1 to 8 carbon atoms such as methyl group, ethyl group, propyl group, isopropyl group, butyl group, isobutyl group, s-butyl group, t-butyl group, pentyl group, hexyl group, heptyl group, octyl group, cyclopentyl group, cyclohexyl group, cycloheptyl group, cyclooctyl group and the like; an alkenyl group having 2 to 8 carbon atoms such as vinyl group, allyl group, crotyl group, prenyl group, 5-hexenyl group, 6-heptenyl group, 7-octenyl group, cyclohexenyl group, cyclooctenyl group and the like; an aryl group having 6 to 20 carbon atoms such as phenyl group, tolyl group, xylyl group, cumenyl group, mesityl group, 2,6-diisopropylphenyl group, naphthyl group, indenyl group, biphenylyl group, biphenylenyl group, phenanthryl group, anthracenyl group, tetracenyl group and the like; an aralkyl group having 7 to 20 carbon atoms such as benzyl group, naphthylmethyl group, indenylmethyl group, biphenylylmethyl group and the like, and the like can be mentioned. As the functional group, for example, an alkoxyl group such as methoxy group, ethoxy group, isopropoxy group and the like (preferably an alkoxyl group having 1 to 8 carbon atoms); amino group; cyano group; hydroxyl group; keto group; carboxyl group and the like can be mentioned.

As representative examples of the alcohol, methanol, ethanol, 1-propanol, 2-propanol, 2-methyl-1-propanol, 1-butanol, 2-butanol, pentanol, isoamyl alcohol, cyclopentanol, hexanol, 2-hexanol, cyclohexanol, heptanol, octanol, 2-octanol, 3-octanol, benzyl alcohol, phenethyl alcohol, phenol, ethylene glycol, diethylene glycol, propylene glycol, ethylene glycol monomethyl ether, ethylene glycol monoethyl ether, diethylene glycol monomethyl ether, diethylene glycol monoethyl ether, propylene glycol monomethyl ether, propylene glycol monoethyl ether and the like can be mentioned. As the alcohol, alkyl alcohol having 1 to 8 carbon atoms is preferable, and alkyl alcohol having 1 to 4 carbon atoms is more preferable.

The telomerization reaction in the present invention is carried out by mixing a palladium compound, isocyanide (I) and base (II) in an alcohol as starting material to form a catalytically active species, and adding a conjugated diene compound as starting material.

The amount of the palladium compound to be used is preferably in the range of 0.0000001-0.00002 equivalent, more preferably in the range of 0.000001-0.00002 equivalent, per a conjugated diene compound. When the amount of the palladium compound to be used exceeds 0.00002 equivalent per a conjugated diene compound, the economic aspect is degraded and recovery operation becomes complicated due to the precipitation by a reductive coupling of the palladium compound, which is industrially unpreferable.

The amount of the isocyanide (I) to be used is preferably in the range of 0.1-50 equivalents, more preferably in the range of 1-20 equivalents, per a palladium compound. The amount of the base (II) to be used is preferably in the range of 0.1-100000 equivalents, more preferably in the range of 1-10000 equivalents, per a palladium compound. The amount of the alcohol to be used is preferably in the range of 0.1-10 equivalents, more preferably in the range of 0.5-5 equivalents, per a conjugated diene compound.

The telomerization reaction system in the present invention can use a solvent as long as the reaction is not inhibited. As the solvent, for example, hydrocarbons such as butane, isobutane, butene, isobutene, pentane, hexane, cyclohexane, benzene, toluene, xylene and the like; halogenated hydrocarbons such as dichloromethane, 1,2-dichloroethane, chloroform and the like; sulfur-containing compounds such as dimethyl sulfoxide, sulfolane and the like; ether compounds such as tetrahydrofuran, dipentyl ether, dihexyl ether, diheptyl ether, dioctyl ether, hexylpentyl ether, diphenyl ether, di(p-tolyl) ether, di(m-tolyl) ether, di(o-tolyl) ether, di(2,3-dimethylphenyl) ether, di(2,6-dimethylphenyl) ether, di(2,4,6-trimethylphenyl) ether, (2-chloroethyl) phenyl ether, (2-bromoethyl) phenyl ether, 1,2-dimethoxybenzene, 1,2,3-trimethoxybenzene, 3,4,5-trimethoxytoluene, 1-methoxynaphthalene, 2-methoxynaphthalene, 1,2-dimethoxynaphthalene, diethylene glycol diethyl ether, diethylene glycol diisopropyl ether, diethylene glycol di-n-butyl ether, dipropylene glycol dimethyl ether, dipropylene glycol diisopropyl ether, dipropylene glycol di-n-butyl ether, triethylene glycol dimethyl ether, triethylene glycol methyl vinyl ether, tetraethylene glycol dimethyl ether, tetraethylene glycol diethyl ether, polyethylene glycol dimethyl ether (average molecular weight 400), polyethylene glycol dimethyl ether (average molecular weight 2000), polyethylene glycol diethyl ether (average molecular weight 400), polyethylene glycol divinyl ether (average molecular weight 240), 12-crown-4,15-crown-5, 18-crown-6, dicyclohexyl-18-crown-6 and the like; amides such as formamide, acetamide, N-methylformamide, N-ethylformamide, N,N-dimethylformamide, N,N-diethylformamide, N-methylacetamide, N-ethylacetamide, N,N-dimethylacetamide, N,N-diethylacetamide, propionamide, N-(1-cyclohexenyl) formamide, N-(2-pyridyl) formamide, N-(3-methyl-2-pyridyl) formamide, N-methyl-N-(2-pyridyl) formamide, N-(3-methoxypropyl) formamide, diphenylformamide, 1-methyl-2-pyrrolidinone, 1-ethyl-2-pyrrolidinone and the like, and the like can be mentioned. These solvents may be used alone, or in a mixture of two or more kinds thereof. While the amount of the solvent to be used is not particularly limited, it is preferably in the range of 0.001-1000 equivalents per a conjugated diene compound.

The reaction temperature of the telomerization reaction is preferably in the range of 0° C. to 1500° C., more preferably in the range of 200° C. to 110° C. When the reaction temperature is low, the reaction time becomes longer, and when the reaction temperature is high, by-products increase. While the reaction pressure is not particularly limited and the reaction can be carried out within the range of from normal pressure to pressurization, the reaction is generally carried out under a pressure created at a reaction temperature.

The reaction time of the telomerization reaction is not particularly limited and it is generally 0.01-30 hrs, preferably 0.1-20 hrs.

The present invention can be performed in both a batch process and a continuous process. In the case of a continuous process, both a piston flow reactor and a continuous stirred tank reactor can be employed and they may be used in combination.

After the completion of the reaction, a telomerization reaction product can be separated from the obtained reaction mixture by a conventional method. For example, a solvent and an unreacted starting material are separated by distillation and, as necessary, the residue is purified by distillation, recrystallization, reprecipitation or column chromatography to give the object product. These separation methods may be performed independently or in combination. In addition to the above-mentioned purification operation, the catalyst is separated as necessary. As a separation method of the catalyst, an evaporation method, a thin layer distillation method, a layer separation method, an extraction method, an adsorption method and the like are employed. These methods may be performed independently or in combination.

For example, a reaction scheme of telomerization reaction according to the production method of the present invention when 1,3-butadiene is used as a conjugated diene compound is shown below.

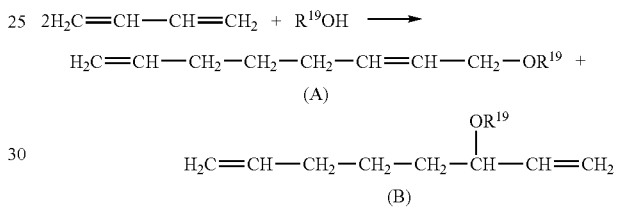

In the above-mentioned telomerization reaction, 3-position substituted ether (B) is produced in addition to 1-position substituted ether (A).

According to the production method of the present invention, an ether product (A) wherein an alcohol is added to the terminal can be produced with high regioselectivity (straight chain selectivity). Moreover, the following advantages are afforded. (1) The selectivity of telomerization reaction is high, and the production amount of byproducts other than ethers such as 1,3,7-octatriene, 4-vinylcyclohexene and the like is small. (2) The conversion ratio of the conjugated diene compound is high, and the yield of the object compound is high. (3) TOF (turnover frequency) is high, the yield per unit amount of the catalyst and the yield per reaction time are high, namely, the catalytic activity is high.

EXAMPLES

The present invention is explained in detail by referring to Examples, which are not to be construed as limitative. In Examples and Comparative Examples, TOF, conversion ratio of butadiene, straight chain selectivity and telomerization selectivity are defined as follows, wherein yield is shown in %.

$TOF$=[{(yield of 1-methoxy-2,7-octadiene)+(yield of 3-methoxy-1,7-octadiene)+(yield of 1,3,7-octatriene)+(yield of 4-vinylcyclohexene)}/100]× 100,000 (molar ratio of 1,3-butadiene and palladium compound before reaction)/2 (hr)

conversion ratio of butadiene=[{(number of mol of 1,3-butadiene before reaction)−(number of mol of 1,3-butadiene after reaction)}/(number of mol of 1,3-butadiene before reaction)]×100 straight chain selectivity=[(yield of 1-methoxy-2,7-
octadiene)/{(yield of 1-methoxy-2,7-octadiene)+
(yield of 3-methoxy-1,7-octadiene)}]×100 telomerization selectivity=[{(yield of 1-methoxy-2,7-
octadiene)+(yield of 3-methoxy-1,7-octadiene)}/
{(yield of 1-methoxy-2,7-octadiene)+(yield of
3-methoxy-1,7-octadiene)+(yield of 1,3,7-oc-
tatriene)+(yield of 4-vinylcyclohexene)}]×100

Example 1

To an autoclave having an inner volume of 100 mL were successively added bis(dibenzylideneacetone) palladium (2.0 mg, 3.5 micromol), methanol (30 mL, 0.74 mol), t-butylisocyanide (1.2 mg, 14 micromol), potassium methoxide (24.5 mg, 0.35 mmol) and 1,2,4-trimethylbenzene (1.0 g, internal standard) under an argon atmosphere at room temperature. After feeding 1,3-butadiene (30 mL, 0.35 mol), the mixture was heated to 80° C. After 2 hr and 3 hr, the obtained reaction mixture was analyzed by gas chromatography (Shimadzu Corporation, GC-14B). The results are shown in Table 1.

Example 2

The same reaction and operation as in Example 1 were performed except that 1,1-dimethylpropylisocyanide (1.4 mg, 14 micromol) was used instead of t-butylisocyanide. The obtained reaction mixture was analyzed by gas chromatography (as mentioned above). The results are shown in Table 1.

Example 3

The same reaction and operation as in Example 1 were performed except that 1,1,3,3-tetramethylbutylisocyanide (1.9 mg, 14 micromol) was used instead of t-butylisocyanide. The obtained reaction mixture was analyzed by gas chromatography (as mentioned above). The results are shown in Table 1.

Example 4

The same reaction and operation as in Example 1 were performed except that palladium acetate (0.79 mg, 3.5 micromol) was used instead of bis(dibenzylideneacetone) palladium. The obtained reaction mixture was analyzed by gas chromatography (as mentioned above). The results are shown in Table 1.

Example 5

The same reaction and operation as in Example 1 were performed except that palladium acetylacetonate (1.06 mg, 3.5 micromol) was used instead of bis(dibenzylideneacetone) palladium. The obtained reaction mixture was analyzed by gas chromatography (as mentioned above). The results are shown in Table 1.

Example 6

The same reaction and operation as in Example 1 were performed except that 1,3-butadiene (60 mL, 0.70 mol) was used instead of 1,3-butadiene (30 mL, 0.35 mol). The obtained reaction mixture was analyzed by gas chromatography (as mentioned above). The results are shown in Table 1.

Comparative Example 1

To an autoclave having an inner volume of 100 mL were successively added nickel acetylacetonate (0.9 mg, 3.5 micromol), methanol (30 mL, 0.74 mol), t-butylisocyanide (1.2 mg, 14 micromol), potassium methoxide (24.5 mg, 0.35 mmol) and 1,2,4-trimethylbenzene (1.0 g, internal standard) under an argon atmosphere at room temperature. After feeding 1,3-butadiene (30 mL, 0.35 mol), the mixture was heated to 80° C. After 2 hr and 3 hr, the obtained reaction mixture was analyzed by gas chromatography (as mentioned above). The results are shown in Table 1.

Comparative Example 2

The same reaction and operation as in Example 1 were performed except that cyclohexylisocyanide (1.53 mg, 14 micromol) was used instead of t-butylisocyanide. The obtained reaction mixture was analyzed by gas chromatography (as mentioned above). The results are shown in Table 1.

Comparative Example 3

The same reaction and operation as in Example 1 were performed except that tetrakis triphenylphosphine palladium (4.04 mg, 3.5 micromol) was used instead of bis (dibenzylideneacetone) palladium. The obtained reaction mixture was analyzed by gas chromatography (as mentioned above). The results are shown in Table 1.

Comparative Example 4

The same reaction and operation as in Example 1 were performed except that t-butylisocyanide (24.0 mg, 280 micromol) was used instead of t-butylisocyanide (1.2 mg, 14 micromol). The obtained reaction mixture was analyzed by gas chromatography (as mentioned above). The results are shown in Table 1.

Comparative Example 5

The same reaction and operation as in Example 1 were performed except that tetrakis (triphenylphosphine) palladium (4.04 mg, 3.5 micromol) was used instead of bis (dibenzylideneacetone) palladium, and cyclohexylisocyanide (1.53 mg, 14 micromol) was used instead of t-butylisocyanide. The obtained reaction mixture was analyzed by gas chromatography (as mentioned above). The results are shown in Table 1.

TOF was calculated based on the gas chromatographic analytical value after 2 hr, and conversion ratio of butadiene, straight chain selectivity and telomerization selectivity were calculated based on the gas chromatographic analytical values after 3 hr.

TABLE 1

| Example | conversion ratio of butadiene (%) | straight chain selectivity (%) | Telomerization selectivity (%) | TOF (h$^{-1}$) |
| --- | --- | --- | --- | --- |
| Example 1 | 100 | 98 | 98 | 40,000 |
| Example 2 | 100 | 97 | 98 | 41,000 |
| Example 3 | 100 | 97 | 98 | 43,000 |
| Example 4 | 100 | 98 | 98 | 41,000 |
| Example 5 | 100 | 97 | 98 | 39,000 |

TABLE 1-continued

| Example | conversion ratio of butadiene (%) | straight chain selectivity (%) | Telomerization selectivity (%) | TOF (h$^{-1}$) |
|---|---|---|---|---|
| Example 6 | 60 | 98 | 98 | 40,000 |
| Comparative Example 1 | 3 | 89 | 90 | 1,000 |
| Comparative Example 2 | 6 | 88 | 92 | 2,000 |
| Comparative Example 3 | 23 | 78 | 91 | 8,000 |
| Comparative Example 4 | 6 | 81 | 95 | 2,000 |
| Comparative Example 5 | 1 | 76 | 88 | 300 |

INDUSTRIAL APPLICABILITY

The composition of the present invention is useful as a catalyst of a telomerization reaction of a conjugated diene compound and an alcohol.

The method of the present invention is employed for producing ethers industrially advantageously from a conjugated diene compound and an alcohol.

This application is based on application Nos. 2003-11847 and 2003-302243 filed in Japan, the contents of which are incorporated hereinto by reference.

The invention claimed is:

1. A method of producing an ether, which comprises subjecting a conjugated diene compound and an alcohol to a telomerization reaction in the presence of a catalyst composition to give an ether, wherein the catalyst composition comprises (i) a palladium compound, (ii) an isocyanide represented by the formula (I)

$$R^1R^2R^3CNC \qquad (I)$$

wherein $R^1$, $R^2$ and $R^3$ are the same or different and each is an optionally substituted alkyl group or two of them optionally form a cycloalkyl group together with a carbon atom bonded thereto, and (iii) a base represented by the formula (II)

$$M(OR^4)_n \qquad (II)$$

wherein M is an alkali metal, an alkaline earth metal, or an onium, $R^4$ is a hydrogen atom, an optionally substituted alkyl group, an optionally substituted alkenyl group, an optionally substituted aryl group, or an optionally substituted aralkyl group, with the proviso that when M is an alkali metal or an onium, then n is 1, and when M is an alkaline earth metal, then n is 2.

2. The production method of claim 1, wherein the alcohol is represented by the formula (VII)

$$R^{19}OH \qquad (VII)$$

wherein $R^{19}$ is an alkyl group optionally having substituents, an alkenyl group optionally having substituents, an aryl group optionally having substituents or an aralkyl group optionally having substituents.

3. The production method of claim 1, wherein the alcohol is selected from methanol, ethanol, 1-propanol, 2-propanol, 2-methyl-1-propanol, 1-butanol, 2-butanol, pentanol, isoamyl alcohol, cyclopentanol, hexanol, 2-hexanol, cyclohexanol, heptanol, octanol, 2-octanol, 3-octanol, benzyl alcohol, phenethyl alcohol, phenol, ethylene glycol, diethylene glycol, propylene glycol, ethylene glycol monomethyl ether, ethylene glycol monoethyl ether, diethylene glycol monomethyl ether, diethylene glycol monoethyl ether, propylene glycol monomethyl ether and propylene glycol monoethyl ether.

4. The production method of claim 1, wherein the palladium compound is a divalent palladium salt.

5. The production method of claim 1, wherein the amount of the palladium compound to be used is within the range of 0.0000001-0.00002 equivalent per the conjugated diene compound.

6. The production method of claim 1, wherein the amount of the isocyanide to be used is within the range of 0.1-50 equivalents per the palladium compound.

7. The production method of claim 1, wherein the reaction temperature of the telomerization reaction is within the range of 0° C.-150° C.

* * * * *